United States Patent [19]
Eckhardt et al.

[11] Patent Number: 5,897,867
[45] Date of Patent: Apr. 27, 1999

[54] **EFFICACIOUS VACCINES AGAINST *BORDETELLA PERTUSSIS* COMPRISING A COMBINATION OF INDIVIDUALLY PURIFIED PERTUSSIS ANTIGENS**

[75] Inventors: Thomas G. Eckhardt, New Windsor; John W. Gotto, Suffern, both of N.Y.; David K. McClintock, Ramsey, N.J.; Jane V. Scott, Chappaqua, N.Y.

[73] Assignee: American Cyanamid Company, Madison, N.J.

[21] Appl. No.: 08/447,150

[22] Filed: May 22, 1995

Related U.S. Application Data

[62] Division of application No. 07/549,236, Jul. 11, 1990, abandoned.

[51] Int. Cl.[6] .......................... A61K 39/05; A61K 39/08; A61K 39/10; A61K 39/102
[52] U.S. Cl. .................. 424/240.1; 424/238.1; 424/239.1; 424/253.1; 424/256.1
[58] Field of Search ............... 424/238.1, 239.1, 424/240.1, 253.1, 256.1

[56] References Cited

U.S. PATENT DOCUMENTS

| | | | |
|---|---|---|---|
| 4,338,299 | 7/1982 | Vesselinova-Jenkins | 424/92 |
| 4,784,589 | 11/1988 | Robinson | 424/9 |
| 5,276,142 | 1/1994 | Gotto | 530/413 |
| 5,578,308 | 11/1996 | Capiau et al. | 424/240.1 |

FOREIGN PATENT DOCUMENTS

| | | | |
|---|---|---|---|
| 101 562 | 2/1984 | European Pat. Off. | A61K 39/02 |
| 101562 | 2/1984 | European Pat. Off. | A61K 39/02 |
| 162 639 | 11/1985 | European Pat. Off. | A61K 39/10 |
| 235 474 | 9/1987 | European Pat. Off. | C12N 15/00 |
| 462 534 | 12/1991 | European Pat. Off. | C12N 15/31 |

OTHER PUBLICATIONS

Blumberg et al., J. Pediatrics, 117, 46–51 (1990).
DeMagistris et al., J. Exp. Med., 168, 1351–1362 (1988).
Mortimer et al., Am. J. Diseases of Children, 144, 899–904 (1990).
Munoz et al., Bordetella pertussis, 45–47 (M. Dekker publ. 1977).
Robinson et al., Infection and Immunity, 40, 523–528 (1983).
Robinson et al., Vaccine, 3, 11–12 (1985).
Rutter et al., Vaccine, 6, 29–32 (1988).
Shahin et al., J. Exp. Med., 171, 63–73 (1990).
Storsaeter et al., Vaccine, 8, 457–461 (1990).
Moxon et al. Lancet 335:1324–1329, 1990.
Coursaget et al. Infection and Immunity 51(3): 784–7, 1986.
Sarnaik et al. Pediatric Infectious Disease Journal 9:181–6, Mar. 1990.
Coulehan et al. Journal of Infectious Diseases 148 (3): 530–4, 1983.
Shahin et al. Journal of Experimental Medicine 171: 63–73, 1990.
Mortimer et al. Journal of Infectious Diseases 161: 473–9, 1990.

*Primary Examiner*—James C. Housel
*Assistant Examiner*—V. Ryan
*Attorney, Agent, or Firm*—Alan M. Gordon

[57] ABSTRACT

This invention is directed to a vaccine for the prevention of disease caused by *Bordetella pertussis* which comprises the pertussis antigens filamentous hemagglutinin, detoxified lymphocytosis promoting factor and a 69 kilodalton outer membrane protein, where said antigens are individually purified prior to being combined to form the vaccine. The invention is further directed to pertussis vaccines where the antigens are combined in any ratio, including ratios not possible in whole cell or co-purified acellular pertussis vaccines. The pertussis antigens may be further combined with other individually purified pertussis antigens, pertussis structural components, adjuvants, stabilizers and non-pertussis vaccine components.

6 Claims, No Drawings

EFFICACIOUS VACCINES AGAINST *BORDETELLA PERTUSSIS* COMPRISING A COMBINATION OF INDIVIDUALLY PURIFIED PERTUSSIS ANTIGENS

This is a divisional of application Ser. No. 07/549,236, filed Jul. 11, 1990 now abandoned.

FIELD OF THE INVENTION

This invention relates to vaccines efficacious against *Bordetella pertussis* which are prepared by individually purifying specific pertussis antigens which are then combined to form the vaccine. In addition, the vaccine may contain pertussis structural components and non-pertussis vaccine components.

BACKGROUND OF THE INVENTION

The bacterium *Bordetella pertussis* is the causative agent of pertussis or whooping cough, a serious and potentially fatal infectious disease of the upper respiratory tract. Pertussis vaccines currently used contain chemically inactivated whole cells of *B. pertussis*. More recently, acellular pertussis vaccines were developed which are based on material obtained by chemical and physical fractionation of *B. pertussis* cultures.

Whole cell vaccines contain the antigenic components necessary to provide protection from pertussis disease and their efficacy in humans is generally well accepted. However, whole cell vaccines also contain components which are not required for protection. Some of these components, such as endotoxin, have been implicated in undesired effects which may occur coincident with pertussis immunization (Bibliography 1).

Acellular vaccines are less complex than whole cell vaccines, because they lack endotoxin, DNA, and cellular components not associated with protection, such as extraneous enzymes and other proteins. However, acellular vaccines, such as that developed by Takeda Chemical Industries, Ltd., Osaka, Japan (2) and the Kanonji Institute, The Research Foundation for Microbial Diseases (Biken) of Osaka University, Japan (3), may also contain more components than necessary to confer protection. In addition, some acellular vaccines are tedious to produce, because of their requisite co-purification procedure (1).

Based on animal protection studies, several *B. pertussis* antigens have been proposed as protective antigens, namely, lymphocytosis promoting factor (LPF, also known as pertussis toxin, which is detoxified before use and is thereafter referred to as pertussis toxoid) (1), histamine sensitizing factor, or islet activating factor (4), filamentous hemagglutinin (FHA) (1), agglutinogens such as fimbriae (5), and outer membrane proteins (1), such as the 69 kilodalton (69K) outer membrane protein (6).

Each of these antigens is able to individually protect animals in one or more animal models. However, animal models are of limited use in predicting efficacy of a pertussis vaccine in humans, because the *B. pertussis* organism is a natural pathogen only in humans (7).

Based on animal data, two acellular vaccines developed by Biken, one containing LPF and FHA, and one containing LPF alone were evaluated in humans (8,9). Overall, the efficacies of these two vaccines were lower than that of whole cell vaccines. The acellular Biken vaccines were only 58–69% (LPF and FHA) or 41–55% (LPF alone) efficacious in conferring protection as compared to the 85–95% efficacy of the whole cell vaccine (8,9). This indicates that other antigens may need to be included to obtain efficacious pertussis vaccines.

SUMMARY OF THE INVENTION

The vaccines of this invention do not contain undesired or extraneous components. In contrast, existing whole cell pertussis vaccines, although generally efficacious, contain undesired components. Current acellular pertussis vaccines, which are also generally efficacious, may contain more components than are necessary to confer protection.

Accordingly, it is an object of this invention to describe efficacious pertussis vaccines which are prepared by individually purifying specific pertussis antigens and then combining the purified antigens to form the vaccine. At a minimum, the vaccine comprises FHA, LPF and the 69K protein.

It is a further object of this invention to describe pertussis vaccines wherein the antigens are combined in any ratio to optimize protection. Thus, the vaccines can have ratios not possible in whole cell or co-purified acellular pertussis vaccines.

It is yet another object of this invention to include additional individually purified pertussis components in the vaccine, such as the 30 kilodalton outer membrane protein and/or one or more agglutinogens such as fimbriae.

It is an additional object of this invention to further improve the efficacy of the above vaccine by including other pertussis structural components. The pertussis antigens may be conjugated to each other or to pertussis structural components.

It is a still further object of this invention to combine the above vaccine with non-pertussis vaccine components to create multivalent vaccines.

DETAILED DESCRIPTION OF THE INVENTION

The present invention relates to pertussis vaccines efficacious in humans which are well suited to commercial scale production, and which represent a significant improvement over the currently available whole cell and acellular vaccines. Purification of specific antigens individually with combination afterwards has several advantages.

Antigens can be combined in any desired ratio, including ratios not possible in whole cell or co-purified acellular vaccines. Thus, an antigen ratio can be chosen which gives the optimal response in humans. This is in contrast to the acellular vaccines which, as fractionated antigen mixtures, have basically a fixed antigen ratio. The Biken two component vaccine has a FHA:LPF ratio of 50:50 (total 100 parts). The Takeda vaccine has a FHA:LPF:69K:agglutinogen ratio of 85:7:7:1. Throughout this application, ratios are based on the proportions of micrograms of antigens contained in a given dose of vaccine. Whole cell vaccines are also limited in the ratios of antigens to the ranges present in the organisms used.

Chemical detoxification procedures which are needed to remove undesired biological activities of LPF can be performed selectively on the LPF antigen alone prior to combining the antigens into a vaccine. The remaining antigens, which do not require a detoxification procedure, are thus not unnecessarily exposed to the chemicals used for detoxification which could reduce their effectiveness as antigens by destroying their structure or conformation which is responsible for their ability to confer protection. In currently available co-purified acellular vaccines, on the other hand, all antigens are subjected to a chemical detoxification procedure. The resulting vaccine of this invention does not contain undesired components such as endotoxin.

When considering vaccine production on a practical commercial scale, the number of antigens in a pertussis vaccine has to be limited. Depending on the effort required for the purification of the individual antigens, three to four antigens may be a limit. It is, however, feasible that inclusion of further antigens might increase vaccine efficacy to some degree.

The antigens included in the vaccines of this invention are identified by analyzing the composition of the Takeda acellular pertussis vaccine described above, which has been found to have good efficacy (81–95%) in humans (10).

In one embodiment of this invention, the vaccine includes LPF, in its non-toxic form (pertussis toxoid), FHA and the 69K protein. In another embodiment of this invention, the vaccine includes LPF, FHA, the 69K protein and a 30 kilodalton (30K) outer membrane protein (11). In addition, agglutinogens such as fimbriae can be included in either of these vaccines.

The individual pertussis components are either purified from native *B. pertussis* using purification procedures which are known in the literature and exemplified below, or through other methods such as the use of recombinant DNA techniques to express the individual components. The antigens are expressed in a suitable host organism such as members of the genus Bordetella, *E. coli*, Haemophilus, Streptomyces spec., *Bacillus subtilis*, yeast, insect (such as baculovirus) or mammalian cell lines, or any other suitable host expression system.

The LPF component is detoxified using a chemical detoxification technique as described in the literature (12, 13,14). Alternatively, LPF may be detoxified by genetic means through the introduction of site-directed mutations which abolish the undesired biological activities of the toxin (15,16).

The individually purified antigens are then blended in the desired ratio to produce the vaccine. The vaccines of this invention may also include physiologically acceptable pertussis structural components. These components may be included for the purpose of avoiding side effects or to enhance the presentation of the antigenic components and thereby improve the efficacy of the vaccine. Examples of such structural components include polysaccharides, lipopolysaccharides, lipids, proteins, glycoproteins and lipoproteins.

The pertussis antigens may be conjugated to each other or to pertussis structural components using conventional techniques. The components may be conjugated directly by reductive amination as described by Anderson (17). Alternatively, the components may be linked through a spacer element such as adipic acid dihydrazide as described by Gordon (18) or 6-aminocaproic acid as described by Hilleman et al. (19).

Other non-pertussis vaccine components can be added by conventional techniques to prepare multivalent vaccines. Multivalent vaccines are desirable, particularly for infants and small children, in that they reduce the number of dosage administrations needed to confer protection against a series of disease organisms. Examples of such other vaccine components include diphtheria toxoid, tetanus toxoid, inactivated polio viruses, *Haemophilus influenzae*, Haemophilus polyribosylphosphate-protein conjugates, *Neisseria meningococcus*, Pneumococcus and hepatitis B.

If desired, the vaccine may also include a pharmaceutically acceptable adjuvant such as aluminum gels, calcium gels, modified muramyl dipeptides, monophosphoryl lipid A, liposomes, time release capsules, polyglycolic acids and polyamino acids. Polyglycolic acids and polyamino acids are also useful for oral delivery of the vaccine. Examples of aluminum gels useful as adjuvants include precipitated aluminum salts such as aluminum phosphate and aluminum hydroxide. Suitable preservatives such as thimerosal, dextran and glycerine can be added to stabilize the final vaccine. If it is desired that the vaccine be in injectable form, immunologically acceptable diluents or carriers may be included in a conventional manner to prepare liquid solutions or suspensions.

The vaccines of this invention are administered by conventional means such as parenteral injection (subcutaneous or intramuscular), as well as by oral or intradermal administration into human beings to elicit an active immune response for protection against infection caused by *B. pertussis*. The dosage to be administered is determined by means known to those skilled in the art.

In order that this invention may be better understood, the following examples are set forth. The examples are for the purpose of illustration only and are not to be construed as limiting the scope of the invention.

EXAMPLE 1

Purification of LPF

LPF is isolated from the culture supernatant of a *B. pertussis* culture using conventional separation methods. For example, using the method described by Sekura et al. (20), LPF is isolated by first adsorbing culture supernatant onto a column containing the dye-ligand gel matrix, Affi-Gel Blue (Bio-Rad Laboratories, Richmond, Calif.). LPF is eluted from this column by high salt, such as 0.75 M magnesium chloride and, after removing the salt, is passed through a column of fetuin-Sepharose affinity matrix composed of fetuin (Gibco Laboratories, Grand Island, N.Y.) linked to cyanogen bromide (CNBr)-activated Sepharose 4B (Pharmacia, Piscataway, N.J.). LPF is eluted from the fetuin column using 4 M magnesium salt either stepwise or with a gradient. The resulting preparation is essentially free from endotoxin and yields a biologically active protein which can be assayed by hemagglutination assay (HA), ADP-ribosylation assay, CHO cell toxicity assay or other conventional methods suitable for determining the biological activity of LPF.

Alternatively, using the method of Irons et al. (21), culture supernatant is adsorbed onto a CNBr-activated Sepharose 4B column to which haptoglobin is first covalently bound. The LPF binds to the adsorbent at pH 6.5 and is eluted from the column using 0.1 M Tris/0.5 M NaCl buffer by a stepwise change to pH 10.

EXAMPLE 2

Detoxification of LPF

LPF purified by either method described in example 1, is then detoxified to remove undesired activities which could cause side reactions of the final vaccine. Any of a variety of conventional chemical detoxification methods can be used such as treatment with formaldehyde, hydrogen peroxide, tetranitro-methane,or glutaraldehyde.

For example, LPF can be detoxified with glutaraldehyde using a modification of the procedure described in Munoz et al. (12), such that the residual biological activities do not pose any safety concern, while the desired immunogenic properties of LPF are still retained. Purified LPF is placed in a solution containing 0.01 M phosphate buffered saline (PBS) (instead of the solution of 20 mM sodium phosphate with 0.5 M NaCl (pH 7.6) used in Munoz). The solution is treated with enough 0.2% glutaraldehyde solution made in the same buffer to bring the concentration of glutaraldehyde to 0.05%. The mixture is incubated at room temperature for two hours, and then enough 0.2 M L-lysine solution (made in the same buffer) is added to bring the concentration of L-lysine to 0.02 M. The mixture is further incubated for two hours at room temperature and then dialyzed for two days against 0.01 M PBS (instead of the 20 mM sodium phosphate buffer containing 0.5 M NaCl and 0.02 M L-lysine (pH 7.6) used in Munoz) to complete the detoxification.

If recombinant techniques (15,16) are used to prepare a LPF mutant molecule which shows no or little biological activity, a milder form of these chemical procedures can be used. For example, a shorter exposure to the chemical, reduced concentration of the chemical, or detoxification at lower temperature may be possible. In some instances, the detoxification step can be omitted altogether.

EXAMPLE 3

Purification of FHA

FHA is purified from the culture supernatant using a modification of the published method of Cowell et al. (22). Growth promoters such as methylated beta-cyclodextrins may be used to increase the yield of FHA in culture supernatants. The culture supernatant is applied to a hydroxylapatite column. FHA is adsorbed onto the column, but LPF is not. The column is extensively washed with Triton X-100 to remove endotoxin. FHA is then eluted using 0.5 M NaCl in 0.1 M sodium phosphate and, if needed, passed through a fetuin-sepharose column to remove residual LPF. Additional purification can involve passage through a Sepharose C1-6B column (Pharmacia, Piscataway, N.J.). FHA is sterilized by passing it through a suitable filter, such as Millex (Millipore Corporation, Bedford, Mass.).

Alternatively, FHA may be purified using monoclonal antibodies to the antigen, where said antibodies are affixed to a CNBr-activated affinity column (23).

EXAMPLE 4

Purification of 69K Outer Membrane Protein

The 69K outer membrane protein is recovered from the bacterial cells, using the procedure described in co-pending, commonly-assigned U.S. Ser. No. 448,777, filed Dec. 11, 1989, which is hereby incorporated by reference.

In summary, the 69K protein is recovered from the bacterial cells by first inactivating the cells with a bacteriostatic agent such as thimerosal. The inactivated cells are suspended in an aqueous medium such as PBS (pH 7–8) and subjected to repeated extraction at elevated temperature (45–60° C.) with subsequent cooling to room temperature or 4° C. The extractions release the 69K protein from the cells. The material containing the 69K protein is collected by precipitation and passed through an Affi-Gel Blue column. The 69K protein is eluted with a high concentration of salt, such as 0.5 M magnesium chloride. After dialysis, it is passed through a chromatofocusing support such as a Polybuffer Exchanger Gel PBE 94 column (Pharmacia). The recovered 69K fractions are sterilized by filtration through a suitable filter such as Millex.

EXAMPLE 5

Preparation of Vaccine

To prepare a final vaccine product of this invention, the purified and sterilized pertussis components prepared according to Examples 1–4 are first combined in aqueous medium containing sodium chloride and sodium phosphate. Then, if desired, aluminum chloride and sodium hydroxide are added in presence of thimerosal preservative, resulting in an adsorbed vaccine which is formed in situ. Alternatively, a preformed adjuvant may be added to the active components, either separately or after the components are combined. In either procedure, if necessary the pH is adjusted with sodium hydroxide to a desired value in the range pH 6.3–7.5. In a preferred embodiment of this invention, the final vaccine has an FHA:LPF:69K ratio of 57:29:14 (or 4:2:1 to be precise).

EXAMPLE 6

Purification of 30K Outer Membrane Protein

The 30K outer membrane protein is recovered from B. pertussis cells by procedures described in the literature (11). In summary, B. pertussis cells are inactivated by thimerosal, suspended in an aqueous solution containing 2 M sucrose, 0.1 M Tris hydrochloride (pH 7.8), 1% sodium EDTA (pH 7.0) and 1.0% lysozyme. The suspension is incubated at 30° C. for one hour. DNase is added to reduce the viscosity which increases due to cell lysis. Centrifugation of the suspension at 20,000×g for one hour at 30° C. gives a supernatant which is adjusted to pH 5.0 with 0.2 M HCl and stored overnight at 4° C. to precipitate out a mixture of proteins. The precipitate is collected by centrifugation at 30,000×g for 15 minutes.

Extraneous materials are removed by adding 2% Triton X-100 in water and mixing, followed by the addition of ethanol. The mixture is incubated overnight at 4° C. and then centrifuged at 9,000×g for 20 minutes. The precipitate is washed with distilled water and the solution is dialyzed for three days against PBS. The 30K protein is then obtained by successive DEAE-Sepharose C1-6B ion exchange chromatography (in a Tris HCl, EDTA, Zwittergent (TEZ) buffer using a 0 to 1 M NaCl gradient for elution) and Sephacryl S-300 gel filtration chromatography (eluting with a TEZ buffer). The 30K protein is sterilized by passage through a suitable filter. The purified 30K protein may then be combined with the components described in Examples 1–4 to form a final vaccine product of this invention using the procedure set forth in Example 5.

BIBLIOGRAPHY

1. Manclark, C. R., et al., pages 69–106, in *Bacterial Vaccines*, Germanier, R., ed., Academic Press (1984).
2. U.S. Pat. No. 4,455,297.
3. Sato, Y., et al., *The Lancet*, 122–126 (Jan. 21, 1984).
4. Yajima, M., et al., *J. Biochem.*, 83, 295–303 (1978).
5. Cowell, J. L., et al., *Infection and Immunity*, 55, 916–922 (1987).
6. Shahin, R. D., et al., "Immune Protection Mediated by the 69K Outer Membrane Protein of *Bordetella pertussis*", page 51, *Abstracts of the 89th Annual Meeting of the American Society for Microbiology* (1989).
7. Kimura, A., et al., *Infection and Immunity*, 55, 7–16 (1990).

8. Marwick, C., *JAMA,* 259, 2057–2059 (1988).
9. Kallings, L. O., *The Lancet,* 955–960 (Apr. 30, 1988).
10. Mortimer, E. A., Jr., *The Tokai Journal of Expt'l and Clinical Medicine,* 13 Supp., 29–34 (1988).
11. Monji, N., et al., *Infection and Immunity,* 51, 865–871 (1986).
12. Munoz, J. J., et al., *Infection and Immunity,* 33, 820–826 (1981).
13. Relyveld, E. H., et al., *Methods in Enzymology,* 93, 24–60 (1983).
14. Kaslow, H. R., et al., *Biochemistry,* 26, 4397–4402 (1987).
15. Zealey, G., et al., *Vaccines '89,* 259–263 (1989).
16. Pizza, M., et al., *Science,* 246, 497–500 (1989).
17. U.S. Pat. No. 4,673,574.
18. U.S. Pat. No. 4,496,538.
19. U.S. Pat. No. 4,459,286.
20. Sekura, R. D., et al., *J. Biol. Chem.,* 258, 14647–14651 (1983).
21. Irons, L. I., et al., *Biochimica et Biophysica Acta,* 580, 175–185 (1979).
22. Cowell, J. L., et al., *Seminar in Infectious Diseases,* 4, 371–379 (1982).
23. Selmer, J. C., *Acta Path. Microbiol. Immunol. Scand. Sect. C,* 92, 279–284 (1984).

We claim:

1. A multivalent vaccine which comprises:
   (a) a vaccine efficacious in preventing disease caused by *Bordetella pertussis*, wherein antigens of said vaccine comprise Bordetella antigens consisting of: *Bordetella pertussis* antigens filamentous hemagglutinin (FHA), detoxified lymphocytosis promoting factor (LPF) and 69 kilodalton outer membrane protein, and wherein said pertussis antigens are individually purified prior to being combined to form said vaccine, and (b) an *Haemophilus influenzae* polyribosyl phosphate-protein conjugate vaccine.

2. The multivalent vaccine of claim 1 which further comprises diphtheria toxoid and tetanus toxoid.

3. The multivalent vaccine of claim 1 which further comprises at least one of an adjuvant, diluent or carrier.

4. The vaccine of claim 3 wherein the adjuvant is a precipitated aluminum salt such as aluminum phosphate or aluminum hydroxide.

5. The multivalent vaccine of claim 1 which further comprises at least one of a stabilizer or preservative.

6. The vaccine of claim 5 wherein the stabilizer is thimerosal.

* * * * *